United States Patent
Lesinski et al.

(10) Patent No.: US 8,192,488 B2
(45) Date of Patent: Jun. 5, 2012

(54) IMPLANTABLE THERAPEUTIC APPLIANCE FOR THE COCHLEA

(75) Inventors: S. George Lesinski, Cincinati, OH (US); Armand P. Neukermans, Portola Valley, CA (US); Richard L. Grant, Cincinnati, OH (US); Kevyn Irving, Mason, OH (US)

(73) Assignee: Otokinetics Inc., Salt Lake City, UT (US)

( * ) Notice: Subject to any disclaimer, the term of this patent is extended or adjusted under 35 U.S.C. 154(b) by 1302 days.

(21) Appl. No.: 11/886,134

(22) PCT Filed: May 22, 2006

(86) PCT No.: PCT/US2006/010673
§ 371 (c)(1),
(2), (4) Date: Sep. 11, 2007

(87) PCT Pub. No.: WO2006/102555
PCT Pub. Date: Sep. 28, 2006

(65) Prior Publication Data
US 2008/0215148 A1 Sep. 4, 2008

(51) Int. Cl.
*A61F 2/18* (2006.01)
(52) U.S. Cl. .......................................................... 623/10
(58) Field of Classification Search .................. 606/79, 606/80, 180; 604/264; 623/10; 408/230
See application file for complete search history.

(56) References Cited

U.S. PATENT DOCUMENTS

| | | | |
|---|---|---|---|
| 4,071,029 A | 1/1978 | Richmond et al. | |
| 4,880,707 A | 11/1989 | Kohno et al. | |
| 5,273,379 A | 12/1993 | Nishimura | |
| 5,478,093 A | 12/1995 | Eibl et al. | |
| 5,796,188 A | 8/1998 | Bays | |
| 5,951,601 A | 9/1999 | Lesinski et al. | |
| 6,120,484 A | 9/2000 | Silverstein | |
| 6,361,526 B1 | 3/2002 | Reisdorf et al. | |
| 6,689,302 B2 | 2/2004 | Reisdorf et al. | |
| 2005/0171579 A1* | 8/2005 | Tasche et al. ................ 607/57 |

FOREIGN PATENT DOCUMENTS
WO   WO 03/037212 A3   5/2003

* cited by examiner

*Primary Examiner* — Eduardo C Robert
*Assistant Examiner* — David Comstock
(74) *Attorney, Agent, or Firm* — Nixon Peabody LLP (57) ABSTRACT

A set of fenestration burrs, for fenestrating otic capsule bone (34), includes an initial burr (150) and a sequence of fenestration polishing burrs (180). A polishing burr (152, 152l), of each of the burrs (150, 180), carries at least one spiraling flute (166, 166'). Fenestrations (36) piercing the bone (34) formed using the burrs (150, 180) exhibit uniform diameters while excluding bone dust from the inner ear. An implantable casing (72) includes a hollow collar (76) from which projects a hollow sleeve (74) receivable into the fenestration (36). The casing (72) is secured there by at least one prong (92, 102) jutting from the sleeve (74). A therapeutic appliance (134) is insertable into the casing (72). A flange (116) extending from one end of the sleeve (74) carries at least one L-shaped slot (122) open at one end and extending circumferentially around the flange (116).

25 Claims, 3 Drawing Sheets

IMPLANTABLE THERAPEUTIC APPLIANCE FOR THE COCHLEA

TECHNICAL FIELD

Devices and procedures for mounting a therapeutic device such as a microactuator of a implantable hearing aid system into a fenestration through the otic capsule bone, e.g. the lateral wall of the cochlea, to communicate with fluid within the inner ear.

BACKGROUND ART

The hearing portion of the inner ear is enclosed within a hollow, spiral otic capsule bone shaped like a snail shell that is also referred to as the cochlea. The cochlea is a fluid-filled portion of the inner ear that contains nerve endings essential for hearing.

A biologically sealed attachment into the otic capsule bone that is stable and watertight is often desired for various medical devices and therapies. U.S. Pat. No. 5,951,601 ("the '601 patent") and published United States Published Patent Application No. 2005/02033557 A1 ("the U.S. patent application") both respectively describe procedures for attaching a therapeutic device, such as a microactuator, in a fenestration which pierces the otic capsule bone.

The inventions disclosed in the '601 patent and the U.S. patent application exhibit several advantages. A casing locates a therapeutic device very securely, without vibration. In addition, those inventions facilitate removing a therapeutic device if that were to become necessary. Thirdly, together with a precise atraumatic fenestration procedure the casing provides for a very precise location for a therapeutic device such as a microactuator. Thus, the casing ensures a microactuator or other therapeutic device is optimally situated in the cochlea without damaging the delicate structures of the inner ear.

The casings respectively disclosed in the '601 patent and the U.S. patent application are particularly adapted for implantation into a fenestration that pierces a projecting portion of the otic capsule bone called the promontory. As described in the '601 patent and the U.S. patent application, the casings are adapted for receiving and attaching to a subject a microactuator included in the implantable hearing aid system, a dummy plug to replace the microactuator should its removal become necessary, or any other type of therapeutic device that interacts with fluid or structures within the cochlea. If the casing receives a microactuator, applying an electric signal thereto causes the microactuator to directly stimulate fluid within the inner ear, which stimulation the subject perceives as sound.

A casing for attaching a therapeutic device to a fenestration formed through a subject's promontory in accordance with the respective disclosures of the '601 patent and of the U.S. patent application includes a sleeve having an outer surface. During implantation of the casing, a first end of the sleeve is received into the fenestration. Disposed in that location, the outer surface of the sleeve mates with the fenestration for securing the casing within the fenestration. The hollow sleeve includes an inner surface adapted to receive a barrel of the microactuator.

The casing also includes a flange that is integral with the sleeve. The flange projects outward from the outer surface of the sleeve about a second end of the sleeve that is located distal from the first end. The flange, through contact with the promontory, limits a depth to which the first end of the sleeve may enter into the fenestration.

A casing in accordance with the '601 patent or with the U.S. patent application may employ various means for securing the sleeve within the fenestration such as screwing into the promontory or clamping to the promontory. Similarly, such a casing may fasten the microactuator to the casing in various ways such as by a threaded attachment, with screws, with button-and-socket snap fasteners, or with a slotted tongue-and-groove lock. A casing in accordance with the '601 patent or the U.S. patent application may also include a keyway that receives a mating key formed on the barrel of the microactuator for establishing an orientation of the implanted microactuator.

One difficulty in a procedure for securing a therapeutic appliance into the otic capsule bone is that the attachment be biologically sealed. Another difficulty in a process for securing a biologically sealed therapeutic appliance to the cochlea is safely fenestrating the otic capsule bone, particularly the tiny promontory. For example, the maximum diameter of a fenestration piercing the otic capsule bone is approximately 1.0 to 1.5 mm. Furthermore, fenestrating the otic capsule bone must be accomplished without damaging the membranous labyrinth or organ of corti enclosed within the otic capsule bone, i.e. without damaging hearing.

DISCLOSURE

An object is to facilitate attachment of a therapeutic appliance, such as a microactuator or micropump for delivering a drug or therapeutic agent, electrodes etc., in a fenestration formed through a subject's otic capsule bone of the cochlea, particularly the promontory thereof.

Another object is to facilitate removing a therapeutic appliance, such as a microactuator or micropump for drug or therapeutic agent delivery device, electrodes etc., from a fenestration formed through a subject's otic capsule bone of the cochlea, particularly the promontory thereof.

Another object is to provide an easily implanted casing for securely attaching a therapeutic appliance such as a microactuator of an implantable hearing aid system to a fenestration formed through a subject's promontory.

Yet another object is to provide surgical burrs that permit safely fenestrating the lateral wall of the otic capsule bone adjacent to the scala tympani of the cochlea without damage to the membranous labyrinth or organ of corti and thus, without damage to hearing.

Briefly, in one aspect disclosed is a set of fenestration burrs that includes an initial fenestration burr and a sequence of fenestration polishing burrs. The set of fenestration burrs is adapted for use in conjunction with a microdrill for forming a cylindrically-shaped fenestration through a wall of a cochlea of a subject.

The initial fenestration burr includes an elongated shaft one end of which is adapted to be secured to the microdrill for rotating the initial fenestration burr while being used for forming the fenestration. A polishing burr is located along the shaft at a distal end of the shaft furthest from the end thereof that is adapted to be secured into the microdrill. The polishing burr has a cylindrically-shaped outer surface which carries at least one recessed, spiral-shaped flute. The initial fenestration burr also includes a washer-shaped initial burr collar that is:

1. larger in diameter in a direction orthogonal to the shaft than a diameter of the polishing burr in a direction orthogonal to the shaft;
2. located along the shaft juxtaposed with a side of the polishing burr that is furthest from the distal end of the shaft;

3. pierced by an aperture that is aligned with the spiral-shaped flute of the polishing burr juxtaposed with the initial burr collar; and
4. adapted to contact an outer surface of the wall of the cochlea during use of the initial fenestration burr in forming the fenestration to thereby limit penetration of the initial fenestration burr into the wall of the cochlea.

Preferably, the polishing burr of the initial fenestration burr has an end face distal from the initial burr collar that carries a projecting, conically-shaped cutting tip. The conically-shaped cutting tip serves to prevent skating of the initial fenestration burr when beginning to drill a fenestration into the cochlea.

Each of the fenestration polishing burrs in the sequence of fenestration polishing burrs includes an elongated shaft one end of which is adapted to be secured to the microdrill for rotating the fenestration polishing burr while being used for forming the fenestration. A polishing burr is located along the shaft at a distal end of the shaft furthest from the end thereof that is adapted to be secured into the microdrill. The polishing burr has a cylindrically-shaped outer surface which carries at least one recessed, spiral-shaped flute. Each polishing burr of the fenestration polishing burrs has a length in a direction parallel to the shaft which exceeds a corresponding length of the polishing burr of the initial fenestration burr. Each fenestration polishing burr also includes a washer-shaped polishing burr collar that is:

1. larger in diameter in a direction orthogonal to the shaft than a diameter of the polishing burr in a direction orthogonal to the shaft;
2. located along the shaft juxtaposed with a side of the polishing burr that is furthest from the distal end of the shaft;
3. pierced by an aperture that is aligned with the spiral-shaped flute of the polishing burr juxtaposed with the polishing burr collar; and
4. adapted to contact an outer surface of the wall of the cochlea during use of the fenestration polishing burr in forming the fenestration to thereby limit penetration of the fenestration polishing burr into the wall of the cochlea.

The respective lengths of the polishing burrs in the direction parallel to the shaft increase progressively for each successive fenestration polishing burr in the sequence of fenestration polishing burrs.

Configured in this way, the set of fenestration burrs are adapted for forming cylindrically-shaped fenestrations through walls of cochlea which exhibit uniform, repeatable diameters. Moreover, the spiral-shaped flutes on the polishing burr respectively of the initial fenestration burr and the sequence of fenestration polishing burrs keep cochlear bone dust out of a subject's inner ear while forming a fenestration.

In another aspect, disclosed is a casing adapted for implantation into a cylindrically-shaped fenestration that pierces a wall of a cochlea of a subject. The casing includes a hollow, cylindrically-shaped collar having a diameter which exceeds a diameter of the fenestration, and from a side of which extends a hollow, cylindrically-shaped sleeve. The hollow, cylindrically-shaped sleeve is adapted to be received into the fenestration, and to be fixed there by at least one prong which has an end that juts outward from the sleeve. Jutting out in this way the prong is adapted for engaging the otic capsule bone surrounding the fenestration to thereby lock the casing in the fenestration.

In yet another aspect disclosed is a therapeutic appliance, e.g. a microactuator or a micropump, adapted for insertion into a sleeve of a casing that is adapted for implantation into and firmly fixing in a cylindrically-shaped fenestration that pierces a wall of a cochlea of a subject. The implanted casing includes a flange extending from one end of the sleeve. The flange is pierced by at least a first L-shaped slot having an open end that is located furthest from a juncture between the flange and an end of the sleeve. A portion of the L-shaped first slot extends circumferentially around the flange. The therapeutic appliance includes a cylindrically-shaped barrel that is adapted for insertion into the sleeve of the casing. The cylindrically-shaped barrel extends outward from one side of a cylindrically-shaped cap that is adapted for insertion into the flange of the casing upon insertion of the barrel into the casing's sleeve. The cap has at least a first pin projecting outward therefrom which is adapted to be received into the circumferential portion of the first slot of the casing when the barrel is fully inserted into the casing's sleeve.

These and other features, objects and advantages will be understood or apparent to those of ordinary skill in the art from the following detailed description of the preferred embodiment as illustrated in the various drawing figures.

BEST MODE FOR CARRYING OUT THE DISCLOSURE

Figure 1:
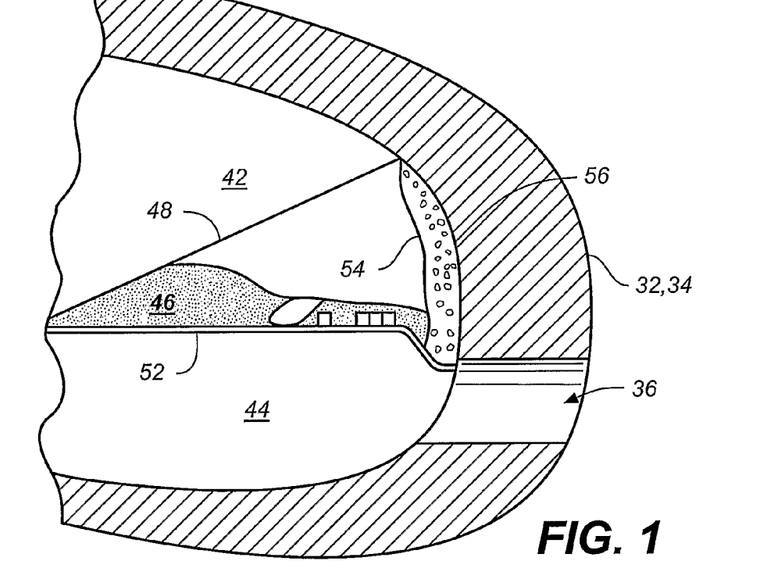
FIG. 1 a cross-sectional view which schematically illustrates a fenestration that pierces the promontory of the cochlea that has been formed with fenestration burrs.

In accordance with the present disclosure, FIG. 1 depicts a promontory 32 portion of a otic capsule bone 34, i.e. cochlea, that is pierced by a fenestration 36. An upper portion of a bony labyrinth within the otic capsule bone 34 is called the scala vestibuli 42, while a lower portion of the bony labyrinth is called the scala tympani 44. A membranous labyrinth within the otic capsule bone 34, called the scala media 46, lies between the scala vestibuli 42 and scala tympani 44. A "vestibular membrane," called Reissner's membrane 48, separates the scala media 46 from the scala vestibuli 42, while a basilar membrane 52 separates the scala media 46 from the scala tympani 44. A stria vascularis 54 and spiral ligament 56 are juxtaposed with an inner surface of the promontory 32. FIG. 1 also illustrates how precise location of the fenestration 36 may advantageously position a microactuator with great precision in the promontory 32 of the otic capsule bone 34. Configured in this way, the fenestration 36 provides a space such that a microactuator or other therapeutic appliance may be introduced into the scala tympani 44 to interact with fluid or structures within the cochlea.

Figure 2:
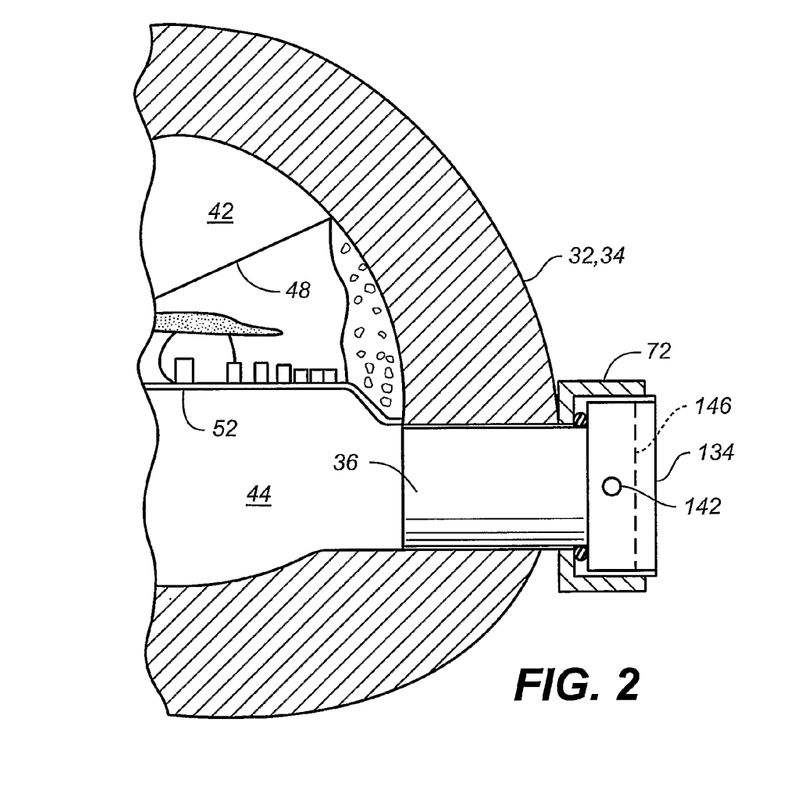
FIG. 2 a cross-sectional view which illustrates a sectioned, prefabricated casing disposed in the fenestration of FIG. 1 that receives and secures a microactuator.

As illustrated in FIG. 2, after the fenestration 36 has been formed through the promontory 32 a unitary, i.e. one piece, casing 72 is inserted and fixed firmly within the promontory 32 of the otic capsule bone 34. Generally it is desirable that over time the casing 72 attach itself permanently to the promontory 32.

Figures 3, 4:
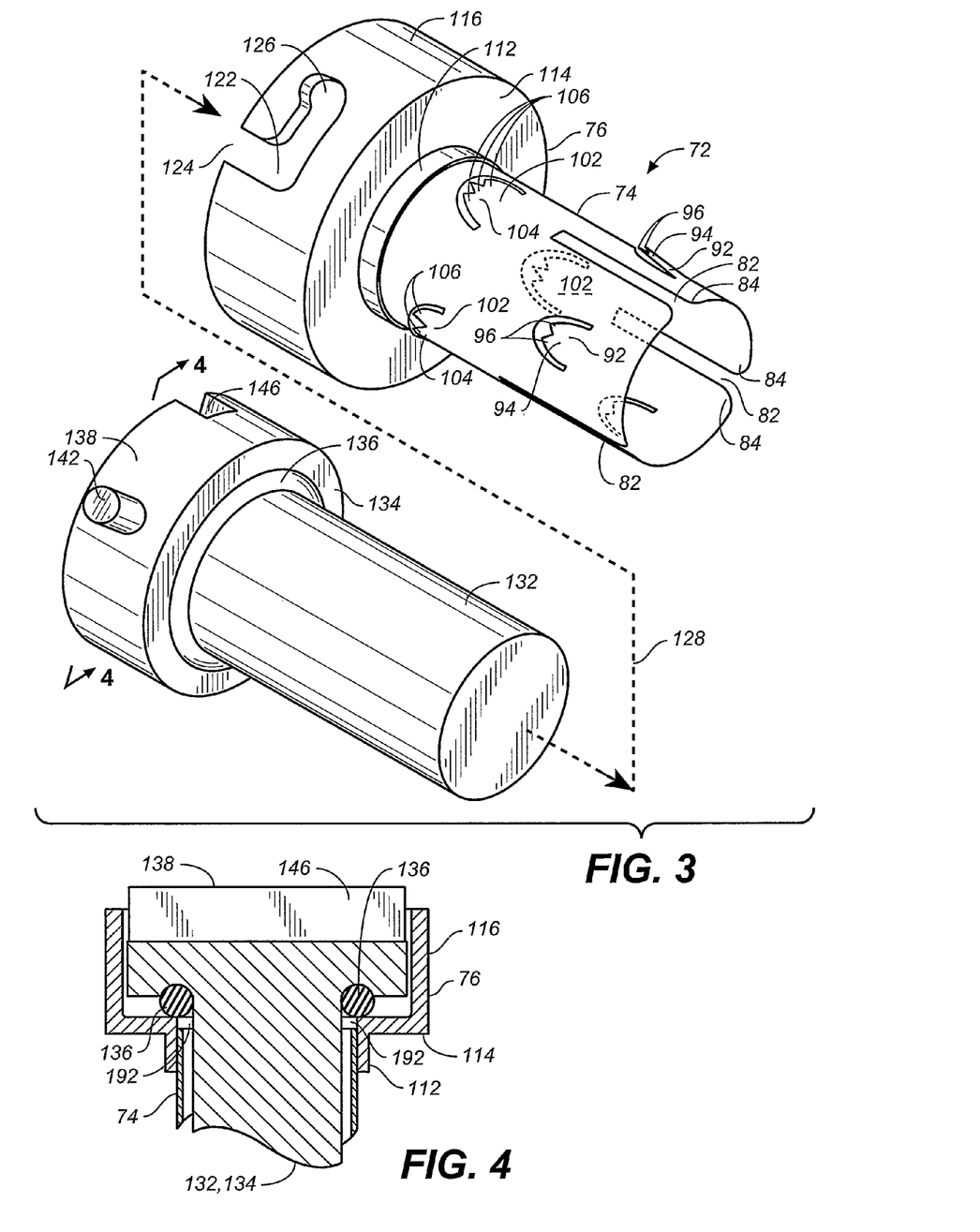
FIG. 3 is a perspective view illustrating a casing having a sleeve which includes a plurality of tined prongs that is adapted for implantation into the fenestration of FIG. 1, and a microactuator adapted for insertion into the casing.
FIG. 4 is a cross-sectional view taken along the line 4-4 of FIG. 3 showing a portion of the mated casing and microactuator depicted in FIG. 3.

Referring now to FIG. 3, the casing 72 preferably includes a hollow, cylindrically-shaped titanium sleeve 74 having a hollow, flanged, cylindrically-shaped titanium collar 76 welded to an end thereof. Three (3) laser cut longitudinal slits 82 spaced equally around the circumference of the sleeve 74 pierce the sleeve 74 from an end thereof extending furthest from the collar 76 along approximately one-half of the sleeve's longitudinal length toward the collar 76. Ends of the slits 82 furthest from the collar 76 preferable have rounded corners 84 to facilitate inserting the sleeve 74 into the fenestration 36.

Other laser cut slits piercing the sleeve 74 preferably establish three spork-shaped (3) prongs 92 respectively located circumferentially about the sleeve 74 between each pair of slits 82. An end 94 of each prong 92 is preferably formed as a pair of tines 96 that are shaped to jut outward from the casing 72. Laser cut slits piercing the sleeve 74 between the slits 82 and the collar 76 establish three (3) more spork-shaped prongs 102 equally spaced around the circumference of the sleeve 74. Each prong 102 is located essentially collinear with one of the slits 82. An end 104 of each prong 102 is preferably formed as three (3) tines 106 that are shaped to jut outward from the casing 72. Configured in this way, the prongs 92, 102 provide the casing 72 with two sets of three (3) barbs with each set of barbs being arranged circumferentially about the sleeve 74. Upon inserting the casing 72 into a properly formed fenestration 36, the prongs 92, 102 engage the otic capsule bone 34 surrounding the fenestration 36 to lock the casing 72 therein.

As best illustrated in FIG. 4, the collar 76 includes a cylindrically-shaped rim 112 which snugly receives the end of the sleeve 74 furthest from the slits 82, and is welded thereto. An annularly-shaped wall 114 of the collar 76 surrounds the rim 112 and the sleeve 74 and projects outward therefrom to a cylindrically-shaped flange 116. The flange 116, which has a diameter that exceeds a diameter of the fenestration 36, is pierced by a pair of L-shaped slots 122, only one of which is visible in FIG. 3. The slots 122 are located diametrically across the flange 116 from each other. Each slot 122 has an open end 124 that is located furthest from the slits 82 of the sleeve 74, i.e. furthest from a juncture between the sleeve 74 and the collar 76. A portion of the slot 122 that extends circumferentially around the flange 116 is formed with an enlarged end 126.

Configured in this way, as indicated by an arrowed line 128 the sleeve 74 of the casing 72 is adapted to receive a cylindrically-shaped barrel 132 of a microactuator 134. An O-ring 136 encircles the barrel 132 at a juncture between the barrel 132 and a cylindrically-shaped cap 138 of the microactuator 134. The cap 138 is formed with a diameter that fits within the flange 116 of the casing 72. A pair of pins 142, only one of which is visible in FIG. 3, project outward from diametrically opposite sides of the cap 138. A slot 146 extends across a face of the cap 138 furthest from the barrel 132. An instrument inserted into the slot 146 facilitates locking the pins 142 into respective ends 126 of the slots 122 when the microactuator 134 is fully inserted into the casing 72. Fully inserting the microactuator 134 into the casing 72 compresses the O-ring 136 between the cap 138 and the wall 114 of the collar 76, and seals therebetween.

Figure 5A:
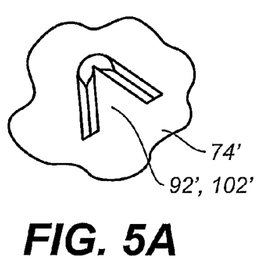
FIGS. 5A, 5B and 5C are plan views of sections of the sleeve of FIG. 3 that illustrate alternative shapes for the prongs that may be substituted for the tined prongs depicted for the sleeve depicted in FIG. 3.
Figure 5B:
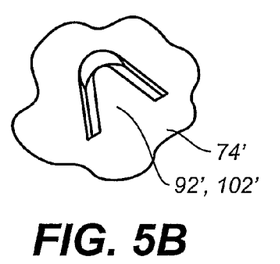
Figure 5C:
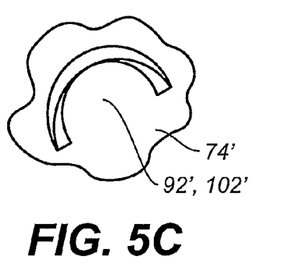

FIGS. 5A, 5B and 5C illustrate alternative shapes for the prongs 92, 102 which may be substituted for the preferred tined shapes depicted in FIG. 3. Those elements depicted in FIGS. 5A, 5B and 5C that are common to the sleeve 74 illustrated in FIG. 3 carry the same reference numeral distinguished by a prime ("'") designation. FIG. 5A depicts a chevron-shaped prong 92', 102' having a pointed end which juts outward from the sleeve 74' to engage the otic capsule bone 34 surrounding the fenestration 36. FIG. 5B also depicts chevron-shaped prong 92', 102' having instead a rounded end which juts outward from the sleeve 74'. FIG. 5C depicts semicircular-shaped prong 92', 102' the curved end which juts outward from the sleeve 74'.

A subject's body usually completes hermetic sealing of the casing 72 and the microactuator 134 to the promontory 32. The endothelial lining of the inner ear and the mucosal lining of the inner ear will migrate across a biocompatible membrane thus sealing the casing 72, microactuator 134 and the fenestration 36, similar to what occurs with the prosthesis following stapedectomy (i.e. fenestration of the stapes).

Other applications exist for the titanium casing 72 in addition to securing the microactuator 134 to the otic capsule bone 34. A micropump can be securely attached to the implanted casing 72 to deliver precisely measured doses of medication directly into the inner ear. For very small volume delivery, the drug delivery system may be shaped similar to the microactuator 134, and enclose a therapeutic agent reservoir right at the otic capsule bone 34. The micropump contains the necessary reservoir of medication when only tiny amounts (microliters) will be delivered from a pulsed piezoelectric mechanism at intervals.

If a larger reservoir of medication is required, a hermetically sealed container made from biocompatible materials (e.g., titanium) may be implanted in the mastoid cavity or subcutaneously. For example, if the drug reservoir is located away from the otic capsule bone 34, a capillary may connect the reservoir to a plug secured in the casing 72 similar to the disclosure of the U.S. patent application. The U.S. patent application is hereby incorporated by reference as though fully set forth here. Accordingly, such a reservoir is connected to an implanted micropump by hollow tubing extending from the mastoid cavity through the facial recess to the dispensing plug located in the casing 72 implanted into the otic capsule bone 34. The micropump is also connected to a programmable signal processor and battery implanted either in the mastoid cavity or subcutaneously with leads extending through the facial recess or antrum. The micropump would be activated by telemetry either for single dose or by signal processor programmed by telemetry to adjust the dosage and frequency of medication delivery to the inner ear. The subcutaneous reservoir may be periodically refilled by transcutaneous injection utilizing sterile techniques.

As disclosed in the U.S. patent application, an approach similar to that described for drug delivery also permits introducing different types of electrodes into the scala tympani 44 which may prove helpful in treating tinnitus, or some forms of nerve deafness.

Figure 6:
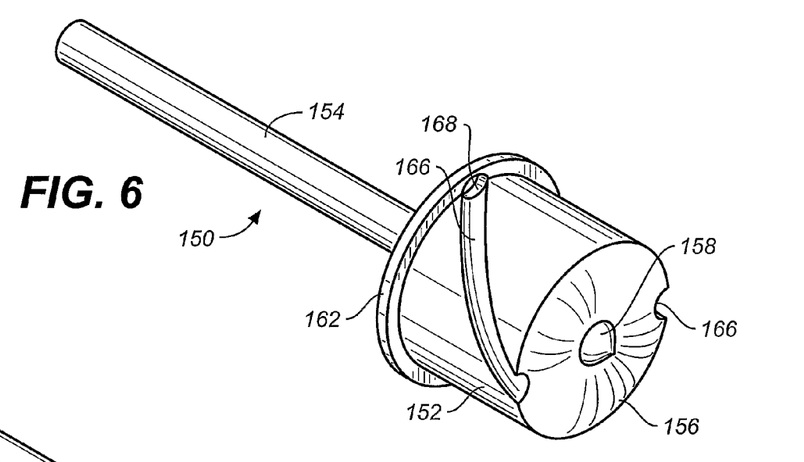
FIG. 6 is a perspective view illustrating a burr used initially in fenestrating the otic capsule bone.
Figure 7:
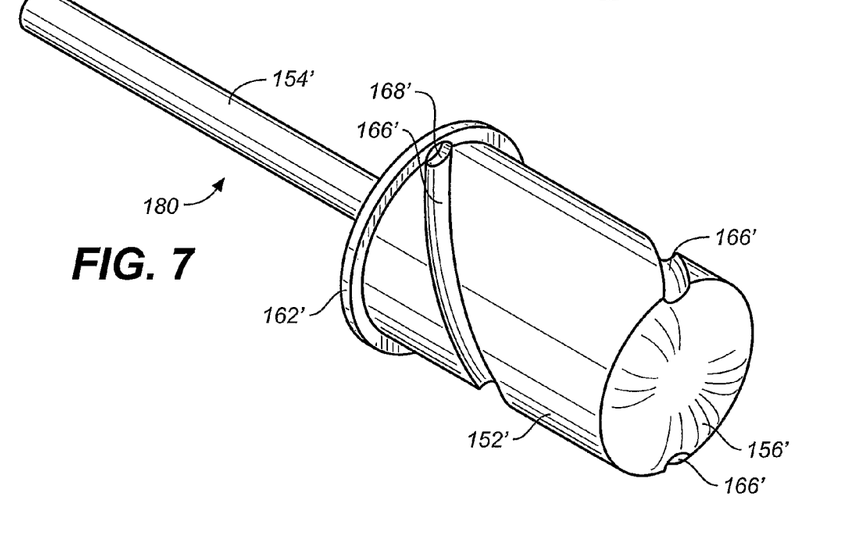
FIG. 7 is a perspective view illustrating one of several similarly shaped burrs used subsequent to the burr depicted in FIG. 6 in fenestrating the otic capsule bone.

Fenestrating the promontory 32 or other area of the otic capsule bone 34 may be safely performed with set of guarded burrs such as those disclosed in the U.S. patent application. However, fenestration burrs of the type illustrated respectively in FIGS. 6 and 7 are preferred for forming the fenestration 36 depicted in FIGS. 1 and 2. Dimensions for the fenestration burrs disclosed herein are derived from the thickness of the promontory 32 at the proposed fenestration site measured for human cochleae.

FIG. 6 depicts a unitary, guarded initial fenestration burr referred to by the general reference character 150. The initial fenestration burr 150 includes a cylindrically-shaped, diamond studded polishing burr 152 that is preferably 1.35 to 1.40 mm in diameter and 1.0 mm long. The polishing burr 152 is located concentrically about and at one end of an elongated shaft 154. The end of the shaft 154 furthest the polishing burr 152 adapts the initial fenestration burr 150 to be received into a microdrill which rotates the burrs while forming the fenestration 36. The initial fenestration burr 150 has a convex end face 156 that protrudes outward away from the shaft 154. A conically shaped cutting tip 158 projects outward from the center of the end face 156 collinear with the shaft 154. The cutting tip 158 prevents skating of initial fenestration burr 150 when beginning to drill a fenestration 36 into the promontory 32. A washer-shaped disk or collar 162, preferably 1.6 mm in diameter and 0.5 mm thick, is located concentrically about the shaft 154 between the polishing burr 152 and the shaft 154. When drilling the fenestration 36, a face of the collar 162 adjacent to the polishing burr 152 contacts an outer surface of the promontory 32 to limit penetration of the initial fenestration burr 150 thereinto.

The polishing burr 152 also preferably includes a pair of flutes 166 recessed into diametrically opposite sides thereof. Each of the flutes 166 spiral about the outer surface of the polishing burr 152 beginning at the end face 156 and extending through an aperture 168 that pierces the collar 162. While drilling into the promontory 32, the flutes 166 extract bone dust from the fenestration 36. Keeping bone dust out of the inner ear prevents foreign body reaction. Also, extracting bone dust consistently produces fenestrations 36 having a uniform, repeatable diameter.

FIG. 7 exemplifies one of a set of a unitary, guarded fenestration polishing burrs referred to by the general reference character 180 that are also used in forming the fenestration 36. Those elements of the polishing burr 180 depicted in FIG. 7 that are common to the initial fenestration burr 150 illustrated in FIG. 3 carry the same reference numeral distinguished by a prime ("'") designation. The significant differences between the initial fenestration burr 150 and the polishing burr 180 are that all fenestration polishing burrs 180:
1. omit the cutting tip 158; and
2. have a longer polishing burr 152'.

Preferably, forming the fenestration 36 employs successive fenestration polishing burrs 180 which in one instance respectively have polishing burrs 152' which are 1.5 mm, 1.75 mm, 2.0 mm and 2.25 mm long. In a presently more preferred instance the polishing burrs 152' of successive fenestration polishing burrs 180 are 1.40 mm, 1.80 mm and 2.20 mm long.

A fenestration 36 formed with the initial fenestration burr 150 and the set of fenestration polishing burrs 180 described herein has a nominal diameter of 1.40 mm. To permit the prongs 92, 102 engage the promontory 32 of the otic capsule bone 34 surrounding the fenestration 36 to lock the casing 72 therein, the sleeve 74 preferably has a diameter of 1.30 mm with a wall thickness of 0.05 mm. The rim 112 of the collar 76 is also preferably formed with a wall thickness of 0.05 mm. Thus the rim 112 fits snugly into and seals with the 1.40 mm diameter fenestration 36. To ensure that the O-ring 136 seals between the collar 76 and the microactuator 134, the collar 76 is preferably welded to the sleeve 74 with a 0.1 mm relief 192 illustrated in FIG. 4.

Industrial Applicability

In general, many if not all of the techniques described above can be used when attaching a microactuator, a micropump, capillary, electrode, or combination microactuator/electrode into a fenestration 36 that pierces the wall of the otic capsule bone 34.

Using such techniques, it is anticipated that conditions such as vertigo, tinnitus, sudden sensorineural hearing loss, endolymphatic hydrops (Ménière's disease), autoimmune inner ear disease, and serous or viral labyrinthitis could be improved by delivering carefully measured doses of a variety of medications (steroids, vasodilators, immune suppressants, anticoagulants, antibiotics, antiviral agents, plasma expanders, antioxidants, etc.) directly into the inner ear. Research has recently discovered that hair cells in the otic capsule bone 34 and vestibular labyrinth of some vertebrates have the ability to regenerate. Perhaps one day it may be possible to deliver a substance (e.g., neurohormone, hair cell DNA actuator) into the inner ear that will stimulate the regrowth of hair cells in the otic capsule bone 34 in patients with sensorineural hearing loss or repair damaged vestibular hair cells.

Another use for the casing 72 disclosed herein is introducing an electrode into the inner ear and securely attaching it to the wall of the cochlea. Application of low dose electrical current can depolarize hair cells or neurons and may someday be used to relieve tinnitus or vertigo triggered by irritable peripheral hair cells or afferent neurons. Some forms of sensorineural hearing loss result from atrophy of the stria vascularis 54 and the associated reduction in the resting cochlear potential across hair cells. A tiny electrode inserted in scala tympani 44 may be able to restore this bioelectric potential and improve this form of nerve deafness.

In each of the applications described above, attaching the microactuator, micropump, or electrode to the titanium casing 72 lining the fenestration 36 enables the surgeon to remove the device with minimal risk of damage to the inner ear. A new device can be inserted to replace an existing one, or an existing device may replaced by a "plug" if the device is no longer needed.

Although the casing 72, sleeve 74, initial fenestration burr 150 and fenestration polishing burrs 180 are described herein in terms of their presently preferred embodiments, it is to be understood that such disclosure is purely illustrative and is not to be interpreted as limiting. Thus, for example while the casing 72 is described as preferably being made from titanium, it may be fabricated from any biocompatible material which exhibits suitable characteristics that permit the prongs 92, 102 to engage the otic capsule bone 34 surrounding the fenestration 36 to lock the casing 72 therein. Similarly, while the casing 72 has been described as being assembled by welding the collar 76 to the sleeve 74, it may also be machined from a single piece of material. Correspondingly, more or fewer than three slits 82 may pierce the sleeve 74 in orientations other than equally spaced, and more or fewer than six (6) prongs 92, 102 may be formed on the sleeve 74 jutting outward therefrom in locations other than those depicted in FIG. 3 and previously described. Similarly, while the casing 72 is described as including two (2) slots 122 diametrically opposed on the flange 116 each of which slots 122 is respectively adapted for receiving one (1) of the pins 142 that project from the cap 138 of the microactuator 134, it is apparent that differing numbers of mating slots 122 and pins 142 may be used in differing but mating orientations respectively on the flange 116 and the cap 138. Also, while the slot 146 formed into the cap 138 of the microactuator 134 is depicted in FIG. 3 as being linear and is described as being adapted for receiving a screwdriver blade, structures having other shapes both depressed into and projecting outward on the cap 138 may be employed to permit locking the pins 142 into respective ends 126 of the slots 122. Analogously, while the initial fenestration burr 150 and the fenestration polishing burrs 180 are described as preferably having diamond studded polishing burrs 152, 152' including their respective end faces 156, 156', their exterior surfaces may be formed by any suitably hard polishing material which consistently produce fenestrations 36 having a uniform, repeatable diameter. Consequently, without departing from the spirit and scope of the disclosure, various alterations, modifications, and/or alternative applications of the disclosure will, no doubt, be suggested to those skilled in the art after having read the preceding disclosure. Accordingly, it is intended that the following claims be interpreted as encompassing all alterations, modifications, or alternative applications as fall within the true spirit and scope of the disclosure.

What is claimed is:

1. A casing configured for implantation into a cylindrically-shaped fenestration that pierces a wall of a cochlea of a subject, the casing comprising:
   a hollow, cylindrically-shaped collar having a diameter which exceeds a diameter of the fenestration; and
   a hollow, cylindrically-shaped sleeve that is:
      configured to be received into the fenestration; and
      fixed at one end to one side of the collar with the remainder of the sleeve extending outward from the collar; and wherein the
      sleeve includes at least one prong having an end that juts outward from the sleeve, the prong configured to engage an otic capsule bone about the fenestration to thereby lock the casing in the fenestration and the sleeve is pierced by at least one slit which begins at an end of the sleeve furthest from the collar and extends along the sleeve toward the collar.

2. A casing configured for implantation into a cylindrically-shaped fenestration that pierces a wall of a cochlea of a subject, the casing comprising:
   a hollow, cylindrically-shaped collar having a diameter which exceeds a diameter of the fenestration; and
   a hollow, cylindrically-shaped sleeve that is configured to be received into the fenestration and fixed at one end to one side of the collar with the remainder of the sleeve extending outward from the collar, wherein the sleeve includes at least one prong having an end that juts outward from the sleeve, the prong configured to engage an otic capsule bone about the fenestration to thereby lock the casing in the fenestration and the sleeve is pierced by at least one longitudinal slit which begins at an end of the sleeve furthest from the collar and extends longitudinally along the sleeve toward the collar.

3. The casing of claim 2, wherein ends of the slit furthest from the collar have rounded corners for facilitating insertion of the sleeve into the fenestration.

4. The casing of claim 2, wherein the slit extends approximately halfway along a longitudinal length of the sleeve toward the collar.

5. The casing of claim 2 wherein the collar includes a cylindrically-shaped rim which snugly receives the end of the sleeve that is fixed to the collar.

6. A casing configured for implantation into a cylindrically-shaped fenestration that pierces a wall of a cochlea of a subject, the casing comprising:
   a hollow, cylindrically-shaped collar having a diameter which exceeds a diameter of the fenestration; and
   a hollow, cylindrically-shaped sleeve that is configured to be received into the fenestration and fixed at one end to one side of the collar with the remainder of the sleeve extending outward from the collar, wherein the sleeve includes at least one prong having an end that juts outward from the sleeve, the prong configured to engage an otic capsule bone about the fenestration to thereby lock the casing in the fenestration and the sleeve is pierced by at least three longitudinal slits each of which respectively begins at an end of the sleeve furthest from the collar and extends longitudinally along the sleeve toward the collar, the longitudinal slits configured to be equally spaced about a circumference of the sleeve.

7. The casing of claim 6 wherein ends of the slits furthest from the collar have rounded corners configured to facilitate insertion of the sleeve into the fenestration.

8. The casing of claim 6 wherein each of the slits extends approximately halfway along a longitudinal length of the sleeve toward the collar.

9. The casing of claim 6 wherein the sleeve includes two more prongs having ends that respectively jut outward from the sleeve, each of the three prongs being located between a pair of the longitudinal slits, each prong configured to engage an otic capsule bone about the fenestration to thereby lock the casing in the fenestration.

10. The casing of claim 6 wherein the sleeve includes two more prongs having ends that respectively jut outward from the sleeve, each of the three prongs disposed respectively between an end of one of the longitudinal slits and the collar, each prong configured to engage an otic capsule bone about the fenestration to thereby lock the casing in the fenestration.

11. The casing of claim 10 wherein the sleeve includes three more prongs having ends that respectively jut outward from the sleeve, each of the prongs disposed between a pair of the longitudinal slits, each prong configured to engage an otic capsule bone about the fenestration to thereby lock the casing in the fenestration.

12. The casing of claim 9, 10, or 11 wherein end(s) of the prong(s) are spork-shaped so each end thereof has tines formed thereat which jut outward from the sleeve.

13. The casing of claim 9, 10, or 11 wherein end(s) of the prong(s) are chevron-shaped with a pointed end jutting outward from the sleeve.

14. The casing of claim 9, 10, or 11 wherein end(s) of the prong(s) are chevron-shaped with a rounded end jutting outward from the sleeve.

15. The casing of claim 9, 10, or 11 wherein end(s) of the prong(s) jutting outward from the sleeve are curved.

16. A casing configured for implantation into a cylindrically-shaped fenestration that pierces a wall of a cochlea of a subject, the casing comprising:
   a hollow, cylindrically-shaped collar having a diameter which exceeds a diameter of the fenestration; and
   a hollow, cylindrically-shaped sleeve that is configured to be received into the fenestration and fixed at one end to one side of the collar with the remainder of the sleeve extending outward from the collar, wherein the sleeve includes at least one prong having an end that juts outward from the sleeve, the prong configured to engage an otic capsule bone about the fenestration to thereby lock the casing in the fenestration and the collar includes an annularly-shaped wall which surrounds the sleeve and projects outward therefrom to a cylindrically-shaped flange.

17. The casing of claim 16 wherein the flange is pierced by at least a first L-shaped slot having an open end that is disposed furthest from the slit of the sleeve, a portion of the first L-shaped slot configured to extend circumferentially around the flange.

18. The casing of claim 17 wherein the flange is pierced by a second L-shaped slot that is disposed about the flange diametrically opposite the first L-shaped slot, the second L-shaped slot having an open end that is located furthest from the slit of the sleeve, a portion of the second L-shaped slot configured to extend circumferentially around the flange.

19. The casing of claim 17 or 18 wherein portion(s) of L-shaped slot(s) configured to extend circumferentially around the flange have enlarged end(s).

20. A kit comprising a casing and a therapeutic appliance, the therapeutic appliance configured for insertion into a sleeve of the casing, the casing configured to be implanted into and firmly fixed in a cylindrically-shaped fenestration that pierces a wall of a cochlea of a subject, the casing comprising:
 a hollow, cylindrically-shaped collar having a diameter which exceeds a diameter of the fenestration;
 a hollow, cylindrically-shaped sleeve that is configured to be received into the fenestration and fixed at one end to one side of the collar with the remainder of the sleeve extending outward from the collar; and wherein the sleeve includes at least one prong having an end that juts outward from the sleeve, the prong configured to engage an otic capsule bone about the fenestration to thereby lock the casing in the fenestration, and wherein the sleeve is pierced by at least one slit which begins at an end of the sleeve furthest from the collar and extends along the sleeve toward the collar; and
 a cylindrically-shaped flange joined to one end of the sleeve, the flange being pierced by at least a first L-shaped slot having an open end that is located furthest from a juncture between the flange and an end of the sleeve, a portion of the first L-shaped slot extending circumferentially around the flange;

and the therapeutic appliance comprising:
 a cylindrically-shaped barrel that is adapted for insertion into the sleeve of the casing; and
 a cylindrically-shaped cap that is joined to one end of the barrel, and that is adapted for insertion into the flange of the casing upon insertion of the barrel into the sleeve of the casing, the cap having at least a first pin projecting outward therefrom which is configured to be received into the circumferential portion of the first L-shaped slot of the casing when the barrel is fully inserted into the sleeve of the casing.

21. The kit of claim 20 wherein the flange is pierced by a second L-shaped slot that is located about the flange diametrically opposite the first L-shaped slot, the second L-shaped slot includes an open end that is disposed furthest from a juncture between the flange and an end of the sleeve, a portion of the second L-shaped slot is configured to extend circumferentially around the flange; and
 the cap of the therapeutic appliance has a second pin projecting outward therefrom which is configured to be received into the circumferential portion of the second L-shaped slot of the casing when the barrel is fully inserted into the sleeve of the casing.

22. The kit of claim 20 or 21 configured for disposing the pin(s) in the L-shaped slot(s) that pierce the flange of the casing by a slot formed on a face of the cap furthest from the barrel that is configured for receiving a screwdriver blade.

23. The kit of claim 20 or 21 wherein the therapeutic appliance includes a microactuator.

24. The kit of claim 20 or 21 wherein the therapeutic appliance includes a micropump.

25. The kit of claim 20 or 21, further comprising:
 an O-ring disposed about the barrel at a juncture between the barrel and the cap configured to effect a seal between the therapeutic appliance and the casing when the barrel of the therapeutic appliance is fully inserted into the sleeve of the casing.

* * * * *

UNITED STATES PATENT AND TRADEMARK OFFICE
CERTIFICATE OF CORRECTION

Page 1 of 1

PATENT NO.        : 8,192,488 B2
APPLICATION NO.   : 11/886134
DATED             : June 5, 2012
INVENTOR(S)       : Lesinski et al.

It is certified that error appears in the above-identified patent and that said Letters Patent is hereby corrected as shown below:

On the Title page, in section (22), replace "May 22, 2006" with --March 22, 2006--.

Signed and Sealed this
Eleventh Day of September, 2012

David J. Kappos
*Director of the United States Patent and Trademark Office*